United States Patent [19]

Fink

[11] Patent Number: 4,873,869

[45] Date of Patent: Oct. 17, 1989

[54] DEVICE FOR THE SCANNING OF OBJECTS BY MEANS OF ULTRASOUND ECHOGRAPHY

[75] Inventor: Mathias Fink, Meudon, France

[73] Assignees: U.S. Philips Corporation; Fujitsu Limited, Japan

[21] Appl. No.: 411,731

[22] Filed: Aug. 26, 1982

[30] Foreign Application Priority Data

Oct. 19, 1981 [FR] France .................. 81 19585

[51] Int. Cl.$^4$ .................................. G01N 29/00
[52] U.S. Cl. .......................... 73/626; 128/660.07
[58] Field of Search ............... 128/660, 599, 602; 73/607, 625-626

[56] References Cited

U.S. PATENT DOCUMENTS 4,414,850 11/1983 Miwa et al. ................. 128/660 X

OTHER PUBLICATIONS

Miwa, Hirohide, "Ultrasonic Measuring Method", European Patent Application filed 4/29/82 published 11/10/82 as No. 0 064 399.
Kuc, R. et al., "Estimating the Acoustic Attenuation Coefficient Slope for Liver from Reflected Ultrasound Signals", IEEE Trans. on Sonics & Ultrasonics, vol. SU-26, No. 5, Sep. 1979, pp. 353-362, (copy 128/660).
Dines, K. A. et al., "Ultrasonic Attenuation Tomography of Soft Tissue", UTS Imaging, vol. 1, No. 1, 1979, (Copy 128/660).

*Primary Examiner*—Jerry W. Myracle
*Attorney, Agent, or Firm*—Jack E. Haken

[57] ABSTRACT

An ultrasonic echography apparatus which comprises a first processing circuit (100) of a known type for the processing of the ultrasonic echos in order to display an A-type echogram on a display device (103), and a second processing circuit (200) which is connected parallel to the first processing circuit and which consists mainly of an amplifier (210), a group of n parallel connected channels (220a ... 220n) each of which comprises at least one band-pass filter (221a ... 221n) and one envelope detector (222a ... 222n), an arithmetic circuit (240) for calculating an indicator for the spread of the amplitudes of the signals of central frequency of each channel, and an evaluation circuit (250) which determines, again for display on the device (103), the value of the ultrasonic attenuation factor in the tissues examined, the evaluation being possible because of the fact that the calculated spread indicator is directly locally correlated to the attenuation factor which is the slope of the curve of the variation of the ultrasonic attenuation as a function of the frequency in the tissues examined.

18 Claims, 4 Drawing Sheets

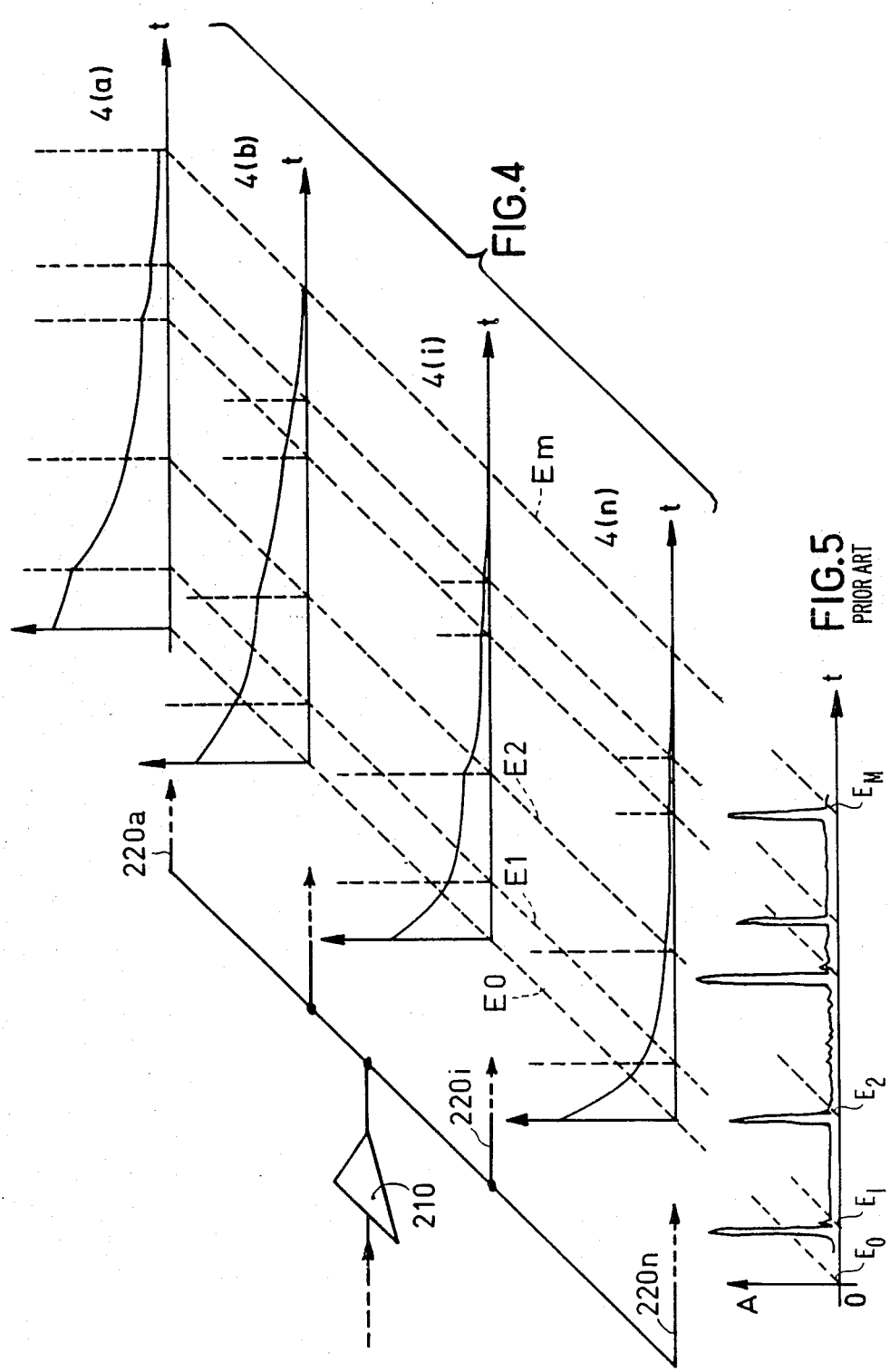

DEVICE FOR THE SCANNING OF OBJECTS BY MEANS OF ULTRASOUND ECHOGRAPHY

FIELD OF THE INVENTION

The invention relates to a device for the scanning of objects, notably biological tissues, by means of ultrasound echography, comprising at least one ultrasonic transducer which is connected to a transmitter stage for the repeated transmission of ultrasonic signals and a receiver stage for receiving the ultrasonic echos corresponding to the most important obstacles encountered by the transmitted signals in their direction of propagation, said receiver stage comprising a first processing circuit for the echos received which consists mainly of a first amplifier which is connected to the output electrode of the ultrasonic transducer, a gain compensation device, and a display device for displaying the positions of the echos in the scanning direction as a function of time as well as the amplitudes thereof. The invention notably relates to an improved receiver stage in such a device which offers the essential advantage that the amount of useful information produced by the ultrasonic image is substantially increased. Such an improvement enables a more accurate and more reliable diagnosis in medical apparatus.

SUMMARY OF THE INVENTION

The device in accordance with the invention is characterized in that the receiver stage comprises a second processing circuit which is connected parallel to the first processing circuit and which consists mainly of:

(A) a second amplifier which is also connected to the output electrode of the transducer;

(B) a group of n parallel channels which are connected to the output of the second amplifier and each of which successively comprises:

(1) a band-pass filter, the relevant pass-bands of the various filters being substantially consecutive and together spanning approximately the pass-band of the second amplifier; and (2) an envelope detector which comprises a rectifier and a low-pass filter having a variable time constant;

(C) an arithmetic circuit which is connected to the output of the n channels and which serves to calculate, on the basis of the output signals thereof, a parameter which is an indicator for the spread of the amplitudes of the signals of central frequency of each of the channels which occurs within the total frequency range of all channels and which is also directly locally correlated to the mean slope $\beta$, being the so-called differential ultrasonic attenuation factor, of the curve of the variation of the ultrasonic attenuation as a function of the frequency in the tissues scanned;

(D) a circuit which is connected to the output of the arithmetic circuit in order to determine the value of the attenuation factor $\beta$ within each of the zones bounded by the echos corresponding to the most important obstacles encountered in the tissues scanned, the output of said circuit being connected to the display device.

For example, in medical applications the customary echography methods produce an ultrasonic image in which only the boundaries between the tissues are clearly visible. Between these boundaries, determined by echos of high amplitude in the A-type echograms, zones are situated which produce less important echos and which are displayed, generally only after dynamic compression operations, in the form of arbitrary grey levels (i.e. levels which are not related in any way to a quantitative information).

The circuitry in accordance with the invention, however, enables very accurate quantitative information to be obtained in these zones in a sense that the proposed second processing circuit performs the local calculation of a parameter which is directly related to the value of the ultrasonic attenuation factor within said zones (said factor being an estimate of the frequency-dependency of the ultrasonic attenuation) with a high resolution. This quantitative information is subsequently used either to enable direct display of the values of the ultrasonic attenuation factor in each of said zones in the scanning direction in A-type echography or in B-type echography to modulate the two-dimensional ultimate image of a plane section of the tissues, for example, by means of a grey scale or a register with different colours. Such a replacement of purely qualitative information by a much finer quantitative image enables the tracing of small variations of the ultrasonic attenuation factor which are due to, for example, the fact that a healthy organ in which this factor has a given value contains a tumor which slightly modifies this value, so that the reliability of the diagnoses can be substantially improved.

THE DRAWINGS

The invention will be described in detail hereinafter with reference to the accompanying drawings, in which:

FIGS. 3 and 4 show the variation in time of the signals in the parallel channels before and after the detection of the envelope, respectively.

FIG. 5 shows an example of a prior art (A-type) echogram originating from the first processing circuit.

A PREFERRED EMBODIMENT

Figure 1:
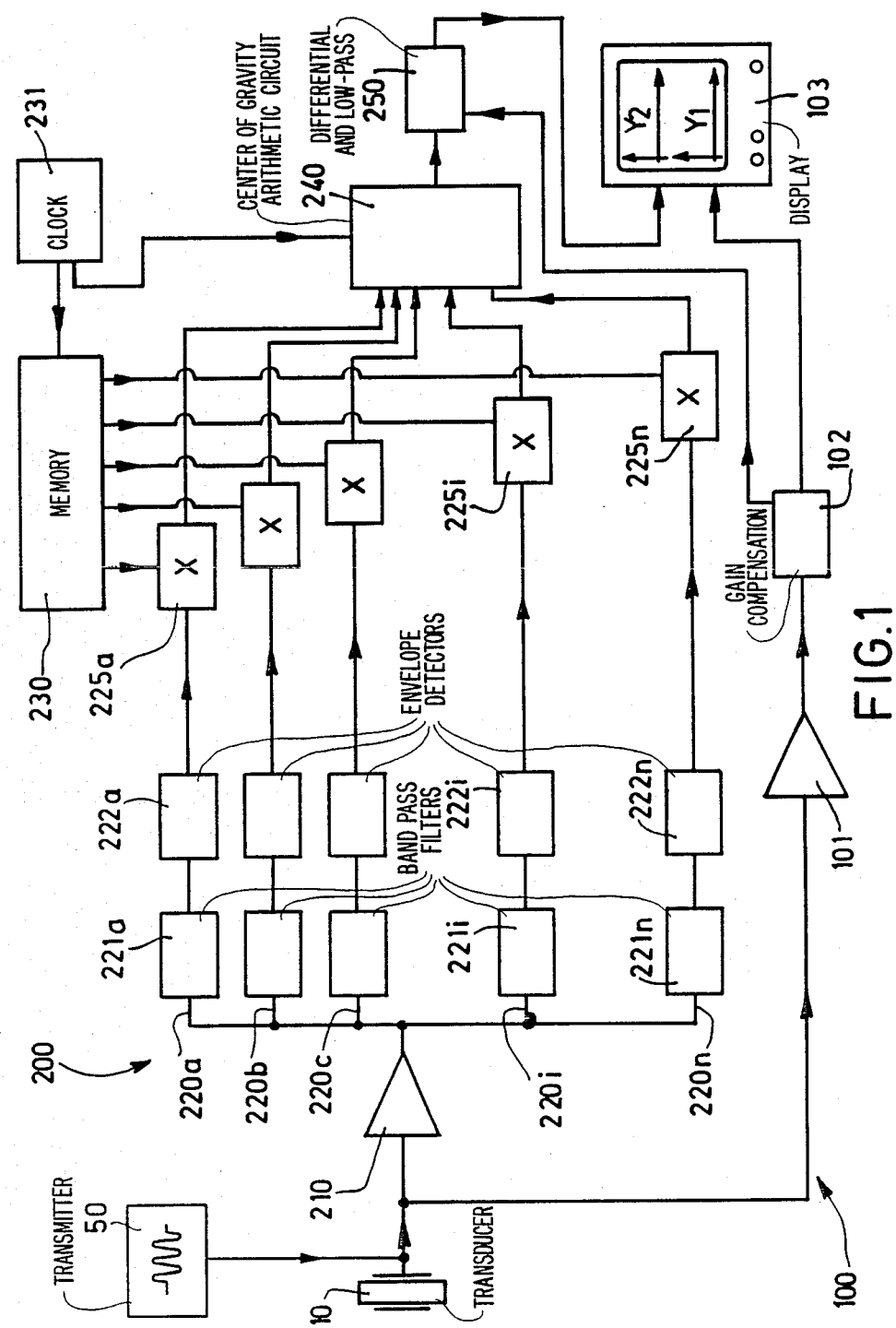
FIG. 1 shows an embodiment of the device in accordance with the invention.

The device described with referene to FIG. 1 comprises a single probe which supports ultrasonic transducer 10 and which can be used to obtain A-type echograms. Evidently, the invention can be used in exactly the same way when instead of only one line a complete plane section of the tissues is examined, either by means of a probe which is connected to a radar-type display device with manual displacement or with so-called mechanical sector scanning, or by means of a linear array of n ultrasonic transducers which define a corresponding number of (p) parallel scanning directions in the tissues to be examined, said array being connected to a switching circuit whereby the echo processing device is successively connected to each activated transducer or group of transducers, or also by means of an array of transducers with so-called electronic sector scanning which is also connected to a switching circuit for switching the processing device and to a network of delay lines or phase shifters.

The transducer 10 is connected on the one side to a transmitter stage 50 which serves to ensure that the transducer can repeatedly transmit ultrasonic signals in an arbitrary scanning direction through the tissues to be examined, and on the other side to a receiver stage which serves for the processing of the ultrasonic echos which are received by the transducer and which correspond to the most important obstacles encountered by the transmitted signals in their propagation direction. The situation of such obstacles is defined in the echograms by the echos of high amplitude which indicate the boundaries between the tissues for which the ultrasonic attenuation factors are to be determined.

The receiver stage comprises in known manner a first processing circuit 100 for the processing of the ultrasonic echos received, said circuit consisting of a first amplifier 101 (which is actually a preamplifier), a gain compensation device 102, and a display device 103. The output electrode of the transducer 10 is connected to the input of the amplifier 101 whose output signals are applied to the gain compensation device 102 whereby the amplitude of the echos is compensated for in dependence of the distance, after which the signals are displayed on the display device 103 in the form of an A-type echogram along an axis which corresponds to the principal propagation direction of the transducer 10.

The receiver stage in accordance with the invention also comprises a second processing circuit 200 which is connected parallel to the first processing circuit 100 and which consists of the following elements:

(A) a second amplifier 210 which also receives the output signal of transducer 10, (B) a group of n mutually parallel channels 220a to 220n which are connected to the output of the amplifier 210 and each of which successively comprises:

(1) a band-pass filter 221a to 221n in which the relevant pass-bands of the various filters are substantially equal and substantially consecutive and together span approximately the pass-band of the second amplifier 210;

(2) an envelope detector 222a to 222n which is identical for each channel and which comprises a rectifier with a subsequent low-pass filter having a time constant which is preferably adjustable to a value which is larger than the mean time interval between the echos of low amplitude which correspond to two adjacent scatter points (the smallest elements in the tissue scanned which still produce echos) in order to reduce the noise which is inherent of the biological object and the inhomogeneities thereof;

(3) a multiplier circuit 225a to 225n which comprises a first input which receives the output signal of the relevant envelope detector and a second input which receives a correction signal from a memory 230 which is controlled by a clock circuit 231. This so-called first correction signal provides compensation for the diffraction effect which occurs in the so-called near field of the transducer due to the fact that the dimensions of the transducer are not infinitely small; the effect of such diffraction is the same as that of a low-pass filter whose cut-off frequency increases as the depth of the echos increases (i.e. as the distance between the most important obstacles and the transducer 10 increases). It follows that said effect decreases as the distance from the transducer increases and that the effect becomes equal to zero in the far field; therefore, the n multiplier circuits 225a to 225n and, of course, the memory 230 which is connected thereto and which supplies the values of the correction signals could be omitted, provided that the tissues to be examined are entirely situated in the far field zone with respect to the transducer used;

(C) an arithmetic circuit 240 which is connected to the output of the n channels 220a to 220n and which calculates, on the basis of the n output signals thereof, a parameter which simultaneously satisfies the following two requirements:

(a) thanks to the method of deriving the information for determining this parameter, the parameter forms an indicator for the spread of the amplitude, occurring within the frequency range of the n channels together, of the signals having the central frequencies of each of the channels;

(b) thanks to this choice of the use of the n output signals, this parameter is directly locally correlated to the mean slope $\beta$ of the curve representing the variation of the ultrasonic attenuation as a function of the frequency in the tissues scanned (the slope $\beta$ being the differential ultrasonic attenuation factor). The parameter which is determined by the circuit 240 in the present embodiment is the center of gravity of the output signals of the n channels 220a to 220n whose variation as a function of time (i.e. of the distance in the scanning direction) satisfies the above requirement (b). In the case of continuous signals, this centre of gravity is defined by the following equation:

$$g(t) = \frac{\int_{f_1}^{f_2} f \cdot H(f, t) \cdot df}{\int_{f_1}^{f_2} H(f, t) \cdot df} \quad (1)$$

in which H (f, t) is the Fourier transform of the frequency sampled signal, and $f_1$ and $f_2$ determine the passband of the transducer. In the case of discrete signals (which is the case herein, because the number n of parallel connected channels is, of course, limited), the equation (1) is replaced by:

$$g(t) = \frac{\sum_{f_a}^{f_n} f_i \cdot |H(f_i, t)|}{\sum_{f_n}^{f_a} |H(f_i, t)|} \quad (2)$$

Thus, it may be stated in brief that in accordance with the invention a kind of representation is continuously available on the output of the n parallel connected channels of the processing device (instantaneous values of the frequency spectrum of the output signal of the transducer 10), each of which is assigned a corresponding value of the center of gravity by the arithmetic circuit 240, so that the variation as a function of time of this centre of gravity can be followed.

Figure 6:
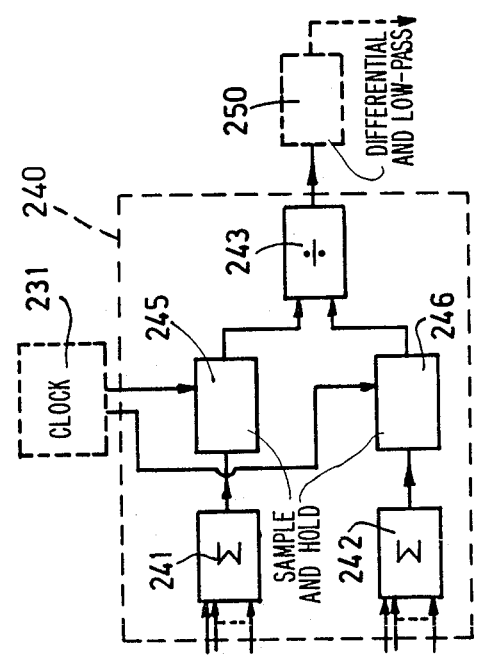
FIG. 6 shows an embodiment of the arithmetic circuit of the device shown in FIG. 1.
Figure 2:
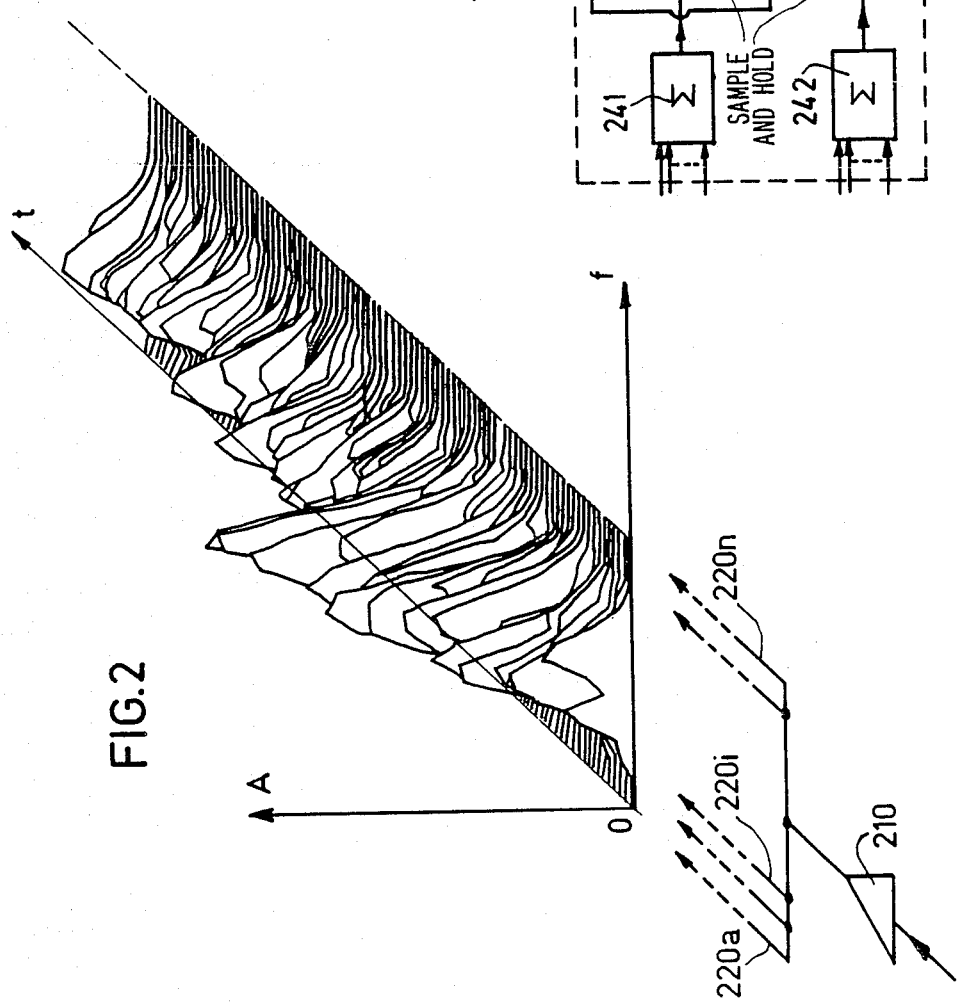
FIG. 2 shows (at discrete points in time) the electronically obtained continuous phenomenon which is formed by the the successive frequency spectra on the output of the n channels of the second processing circuit.
Figure 3:
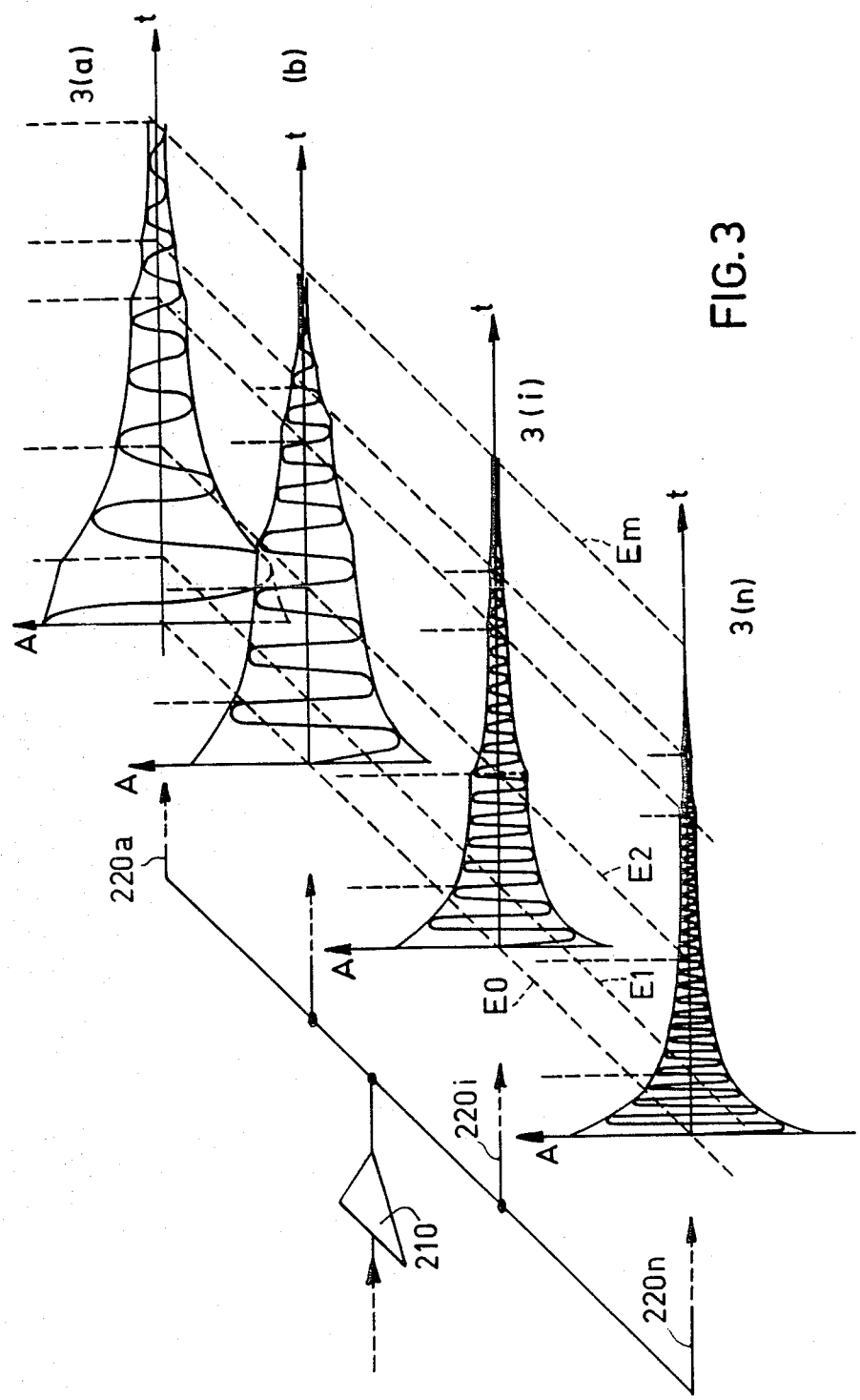

FIG. 2 is a perspective view of such a succession of representation in time, the spectrum of each representation being determined by means of a coordinate system (Of, OA) which is formed by a frequency axis and an amplitude axis (the time axis actually being the axis of propagation of the signals in the n channels 220a to 220n whose "situation" with respect to this perspective view is indicated exclusively for the purpose of illustration in FIG. 2). Utilizing a set of curves 3(a) to 3(n), FIG. 3 shows the variation in time of the output signals of the band-pass filters 221a to 221n before the passage of the signals through the rectifier and low-pass filter in the envelope detectors 222a to 222n; FIG. 4 shows the same signals but on the output of the envelope detectors (the amplifier 210 and the input of the n channels 220a to 220n are again shown in a perspective view in one line with the corresponding curves to the left of the FIGS. 3 and 4. For each curve of the FIGS. 3 and 4, the signals are shown in zones which themselves are bounded by the boundaries Eo to En between the tissues for which the ultrasonic attenuation factors are to be determined, said boundaries corresponding to the echos of high amplitude which are visible in the echogram of the first processing circuit 100 (an example of such an echogram is shown in FIG. 5 in relation to the curves 4(a) to 4(n) of FIG. 4). FIG. 6 shows an embodiment of the arithmetic circuit 240 which comprises a first summing circuit 241 for the n output signals of the channels 220a to 220n, and a second summing circuit 242 for the same output signals, however, weighted by means of a factor which is proportional to the central frequency of each channel 220a to 220n (this weighing operation is made possible by incorporating in the n input channels of the summing circuit 242 n resistors of suitable value and a divider 243 which divides the output signal of the circuit 242 by the output signal of the circuit 241). A sample-and-hold circuit 245, 246 is connected between the output of each circuit 241, 242 and the corresponding input of the divider 243; the circuits 245 and 246 are controlled by the clock circuit 231 and serve to ensure that the signals remain present for a sufficiently long period of time on the input of the divider 243 so that a sufficient amount of time is available for performing the division.

(D) A circuit 250 which is connected to the output of the arithmetic circuit 240 and which serves to determine the value of the ultrasonic attenuation factor $\beta$ within each of the zones bounded within the tissues. The circuit 250 is controlled by the signals supplied via the first processing circuit 100 and is formed by an analog differentiating circuit which is preceded by a low-pass filter for the smoothing of the noise still present on the output signal of the arithmetic circuit 240; this circuit may also be of a numerical type. The correlation between the position of the centre of gravity of the output signals of the n channels and the value of the factor $\beta$ is direct in the far field. Even though this correlation is more complex in the near field due to the previously described diffraction effect, it also becomes direct when the correction is performed which is permitted by the presence of the multiplier circuits 225a to 225n and the memory 230. However, the first correction signals can be applied to the second inputs of the multiplier circuits only if the values to be obtained by these signals in each channel are stored in advance in the memory 230 after a calibration phase (this calibration takes into account the echographic response of the selected transducer when the latter is arranged opposite a reflective metal surface which is successively situated at all distances from the transducer which correspond to the customary depths in echographic examinations). The rhythm at which the first correction signals arrive in each channel is fixed by the clock circuit 231. Taking into account the time constant of the envelope detectors, which is preferably larger than the former value (the mean time interval between echos corresponding to two successive scatter points), the clock period need not be smaller than this time constant; for the present case, tests have resulted in a choice of a clock frequency of 200 kHz which, for example, for an ultrasonic transmission having a duration of approximately 300 microseconds (which corresponds to a tissue depth of approximately 20 cm) requires sixty correction signals to be stored in the memory 230 for each channel Thus, the total number of separate memory locations must be equal to 60n for the total echo processing device. The output signal of the circuit 250 modulates the image displayed on the display device 103. In the present embodiment, this image is composed as follows: it contains on the one hand the known A-type echogram which is supplied by the first processing circuit 100 and which is applied to a first channel $Y_1$ of the display 103, and on the other hand a stepped curve which is shown on a second, vertical channel $Y_2$ and which represents the various values of the ultrasonic attenuation factor $\beta$ between the limits defined by the echogram of the channel $Y_1$, the channel $Y_2$ thus being modulated by the output signal of the circuit 250.

Obviously, the invention is not restricted to the described embodiment; within the scope of the invention many alternatives are feasible. Notably the multiplier circuits 225a to 225n whose function for correcting diffraction effects in the near field of the transducer has already been described, can also be used for correcting the transfer function of this transducer if this function is not Gaussian. This is required because when this transfer function is Gaussian, the formula of the factor $\beta$ (slope of the curve of the variation of the attenuation as a function of the frequency) demonstrates that proportionality exists between $\beta$ and the slope $\Delta f/\Delta t$:

$$\beta \text{ (in dB/cm/MHz)} = \frac{C}{\sigma^2} \times \frac{\Delta f (\text{MHz})}{\Delta t (\mu s)} \qquad (3)$$

in which $\Delta f$ is the frequency variation of the center of gravity, C is a constant factor and $\sigma$, also being constant, is present in the formule H(f) of the spectrum of an echo, when the transfer function of the transducer is Gaussian, in the following form:

$$H(f) = \exp \frac{-(f - f_o)^2}{2\sigma^2} \qquad (4)$$

(in which $f_o$ is the central frequency of the transducer and $\sigma$ is the standard deviation).

It follows from this proportionality that the frequency variation as a function of time of the center of gravity, $\Delta f/\Delta t$, is exactly constant in each of the zones with a fixed factor $\beta$ which are bounded in the tissues by means of the first processing circuit 100. However, if the transfer function of the transducer used is not Gaussian, the curve of the frequency variation of the center of gravity as a function of time is no longer straight and the formula of the mean value of $\beta$ in each zone is much more complex. Thus, the same formula becomes simple again if, in spite of the fact that the transfer function of the transducer is not Gaussian, it can be corrected, for example, again by means of the memory 230 and the multiplier circuits 225a to 225n. The second input of each multiplier circuit then also receives a second correction signal for the correction of this deformation of the transfer function of the transducer 10, said signal again being supplied by the memory 230.

It is also to be noted that an alternative is feasible in which parallel to the calculation circuit 240 there are connected one or more circuits for calculating moments of the frequency spectrum of the output signals of the transducer 10 other than the center of gravity, for example, the second-order moment for studying the variations of the ultrasonic scatter factor as a function of the frequency. Finally, as has already been stated, the invention can be used not only for the scanning of a line (A-type echography), but also for the scanning of a complete plane slice of the tissues to be examined (B-type echography) by means of a manually or mechanically displaced probe, or by means of a known linear array of transducers or an array of transducers with electronic sector scanning. The output signal of the circuit 250 for determining the ultrasonic attenuation factor then ensures that in the display device 103, as the case may be, either a modulation of the image brightness by means of a grey scale takes place, said grey tones being associated with the various values of this factor within each of the zones which are bounded in the tissues examined by the boundaries corresponding to the echos supplied by the A-type echogram of the first processing circuit 100, or a modulation of the image by means of a series of colours which are also associated with the various values of the factor.

What is claimed is:

1. An echo ultrasound scanner comprising:
   transducer means which direct pulses of ultrasound energy into an object, receive echoes of said energy and the produce echo signals corresponding thereto;
   transmitter means which actuate the transducer means to transmit the energy;
   display means which display the positions of the origins of the echoes as functions of the amplitude and time of arrival of the received echoes;
   a first signal processing circuit operably connected to receive the echo signals from the transducer, to compensate the signals for attenuation in the object, and to provide the compensated signals to the display means; and
   a second signal processing circuit operably connected between the transducer means and the display means, which includes:
   (a) a band-pass amplifier connected to amplify the signals from the transducer,
   (b) a group of n parallel channels, each channel comprising:
      (1) a band-pass filter, having an input connected to the output of the band-pass amplifier, the pass-bands of the filters being substantially consecutive and together substantially spanning the pass-band of the band-pass amplifier, and
      (2) an envelope detector which includes a rectifier and a low-pass filter having a variable time constant;
   (c) arithmetic circuit means having inputs connected to outputs of the n channels which calculate, from output signals of the channels, a parameter which is an indicator, over the frequency range of all of the the channels, of the spread of the amplitudes of signals at the central frequency of each of the channels and which is also directly locally correllated to the mean slope $\beta$ of the ultrasonic attenuation in a corresponding region of the object as a function of frequency; and
   (d) means connected to the output of the arithmetic means which determine the value of the attenuation factor and which cause the display means to display a value corresponding to the determined attenuation factor within each of zones which are bounded by the positions corresponding to the origins of selected echoes from the object.

2. A scanner as claimed in claim 1 wherein the time constant of each of the envelope detectors is greater than the quotient of the mean distance between the smallest elements in the object which produce distinct echoes divided by the mean propagation speed of ultrasonic waves in the object.

3. A scanner as claimed in claim 1 or 2 wherein the second signal processing circuit further comprises means for compensating signals in the channels for diffraction effects in the near-field of the transducer, which means comprise
   a memory for storing correction factors and
   n multipliers, each multiplier having a first input connected to the output of the envelope detector in a respective channel, a second input connected to receive correction factors from the memory and an output connected to a corresponding input of the arithmetic circuit means.

4. A scanner as claimed in claim 3 wherein the transfer function of the transducer is non-Gaussian and where the correction factors stored in the memory further compensate for the non-Gaussian transfer function of the transducer.

5. A scanner as claimed in claim 1 wherein the parameter calculated by the arithmetic circuit means is the center of gravity of the output signals of the channels.

6. A scanner as claimed in claim 5, wherein the arithmetic means comprise a first circuit which sums the outputs of the n channels, a second circuit which weights each of the outputs of the n channels by a factor which is proportional to the center frequency thereof and sums the weighted outputs, and a divider which divides the output of the second circuit by the output of the first circuit.

7. A device as claimed in claim 1 wherein the display means display an A-type echogram of signals originating in the first processing circuit and a corresponding stepped curve, the height of which corresponds to the value of ultrasonic attenuation within zones which are bounded by echo signals visible in the A-type echogram.

8. A method for measuring the ultrasonic attenuation in regions of an object comprising the steps of:
   directing pulses of ultrasound energy into the object;
   receiving echo signals representative of echoes of the ultrasound energy from regions within the object;
   detecting the peak value of the envelope of echo signals from a region within each of a plurality of contiguous frequency bands; and
   calculating, from said peak values, a parameter which is an indicator, over the total frequency range of the bands, of the spread of the amplitudes of signals at the center frequency of each of the bands and which is also directly correllated to the mean slope $\beta$ of the ultrasonic attenuation as a function of frequency in the region.

9. The method of claim 8 wherein the ultrasound energy is directed from and received with a transducer and further comprising the step of compensating the detected value in each of the bands by a factor which compensates for diffraction effects in the near field of the transducer.

10. The method of claim 8 wherein the signals are transmitted from and received with a transducer having a non-Gaussian transfer function and further comprising the step of multiplying the detected values by factors which compensate for non-Gaussian transfer function characteristics of the transducer.

11. The method of claim 8, 9 or 10 wherein the step of calculating comprises calculating the center of gravity of the detected values in the bands.

12. The method of claim 11 wherein the step of calculating comprises:
   summing the peak envelope values in all of the bands;
   weighting the peak envelope of each of the bands by a factor which is proportional to the center frequency of the corresponding band;
   summing the weighted values; and
   dividing the sum of the weighted values by the sum of the peak envelope values.

13. A method for measuring the attenuation of ultrasound in an object, comprising the steps of:
   transmitting an ultrasound pulse into the object;
   receiving a reflected ultrasound wave from the object;
   analyzing the spectrum of a first parameter which represents the strength of the reflected wave; and
   calculating a second parameter which is an indicator of the spread of the first parameter as a function of frequency over the entire frequency range of the received wave and which is also directly locally correlated with the slope of the curve of the variation of the ultrasound attenuation in the object as a function of frequency.

14. A method for measuring the attenuation of ultrasound in an object, comprising the steps of:
   transmitting an ultrasound pulse into the object;
   receiving a reflected ultrasound wave from the object;
   analyzing the spectrum of a first parameter which represents the strength of the reflected wave; and
   calculating a second parameter by analysis of the spectrum and obtaining an attenuation slope or other physical characteristics of the object from the second parameter;
   wherein the ultrasonic pulse transmitting step, the reflected wave receiving step and the reflected wave analyzing step are carried out for plurality of directions of ultrasound propagation through the object; and
   generating a distribution diagram of the physical characteristics of the object is obtained by analyzing the spectrum of the first parameter representing the strength of said reflected wave in each direction.

15. An ultrasonic measuring method comprising the steps of:
   transmitting an ultrasonic pulse into an object;
   receiving a reflected wave from said object;
   analyzing the spectrum of a first parameter representing the strength of said reflected wave; and
   obtaining a second parameter by analysis of said spectrum to obtain an attenuation slope or other physical characteristics of said object from said second parameter;
   wherein said second parameter is used as a function of distance or time to obtain its differential or difference coefficient, and said attenuation slope or other physical characteristic is derived therefrom.

16. An ultrasonic measuring method comprising the steps of:
   transmitting an ultrasonic pulse into an object;
   receiving a reflected wave from said object;
   analyzing the spectrum of a parameter representing the strength of said reflected wave; and
   obtaining a center frequency by analysis of said spectrum, to obtain an attenuation slope or other physical characteristics of said object from said center frequency;
   wherein said center frequency is used as a function of distance or time to obtain its differential or difference coefficient, and said attenuation slope or other physical characteristics are derived therefrom.

17. An ultrasonic measuring method according to claim 16 wherein said ultrasonic pulse transmitting step, said reflecting wave receiving step and said reflected wave analyzing step are carried out in accordance with scanning of said object; and, by analyzing the spectrum of said parameter representing the strength of said reflected wave obtained by said scanning, a distribution diagram of the physical characteristics of said object.

18. An ultrasonic measuring method comprising the steps of:
   transmitting an ultrasonic pulse to an object;
   receiving a reflected wave from said object;
   analyzing the spectrum of a parameter representing the strength of said reflected wave; and
   obtaining a center frequency by the analysis of said spectrum to obtain an attenuation slope or other physical characteristics of said object from said center frequency;
   wherein said ultrasonic pulse transmitting step, said reflecting wave receiving step and said reflected wave analyzing step are carried out in a plurality of directions of said object; and a distribution diagram of the physical characteristics of said object is obtained by analyzing the spectrum of said parameter representing the strength of said reflected wave in each direction.

* * * * *